United States Patent
James et al.

(10) Patent No.: US 8,703,218 B2
(45) Date of Patent: Apr. 22, 2014

(54) CHOCOLATE HAVING CHOLECALCIFEROL AND METHOD FOR FORMING

(75) Inventors: Dustin Garth James, St. Louis, MO (US); Helen Kim-James, St. Louis, MO (US)

(73) Assignee: Enteral Health and Nutrition, LLC, St. Louis, MO (US)

(*) Notice: Subject to any disclaimer, the term of this patent is extended or adjusted under 35 U.S.C. 154(b) by 0 days.

(21) Appl. No.: 13/337,593

(22) Filed: Dec. 27, 2011

(65) Prior Publication Data

US 2012/0322774 A1    Dec. 20, 2012

Related U.S. Application Data

(60) Provisional application No. 61/527,702, filed on Aug. 26, 2011, provisional application No. 61/498,778, filed on Jun. 20, 2011.

(51) Int. Cl.
   *A23L 1/30*    (2006.01)
   *A23G 1/00*    (2006.01)

(52) U.S. Cl.
   USPC ............ 426/73; 426/72; 426/531; 426/593

(58) Field of Classification Search
   USPC ................... 426/72, 73, 531, 593
   See application file for complete search history.

(56) References Cited

U.S. PATENT DOCUMENTS

| | | |
|---|---|---|
| 2010/0330151 A1 | 12/2010 | Freeland et al. |
| 2011/0033578 A1* | 2/2011 | Lang ........................ 426/73 |
| 2011/0033579 A1 | 2/2011 | Lang |
| 2011/0060039 A1 | 3/2011 | Bernaert et al. |
| 2011/0189376 A1 | 8/2011 | Elejalde et al. |
| 2011/0274813 A1* | 11/2011 | Kowalczyk et al. ........ 426/579 |

FOREIGN PATENT DOCUMENTS

| | | |
|---|---|---|
| WO | WO 03059358 A1 * | 7/2003 |
| WO | WO 2010081748 A2 * | 7/2010 |

OTHER PUBLICATIONS

Evidence: converter between IU and mg (http://www.etoolsage.com/converter/IU_Converter.asp), downloaded on Mar. 22, 2013.*
Evidence: converter between calorie and gram (http://www.convertunits.com/from/calorie/to/mg), downloaded on Mar. 22, 2013.*
"What is an Emulsifier" (birchhillhappenings.com/aromatip/7910emulsifier.htm, last visit Jul. 15, 2013).*

* cited by examiner

*Primary Examiner* — Ernst Arnold
*Assistant Examiner* — Kyung Sook Chang
(74) *Attorney, Agent, or Firm* — Linda L Lewis; CreatiVenture Law, LLC

(57) ABSTRACT

A method for forming chocolate having cholecalciferol is provided. The method includes mixing cholecalciferol into an oil to produce a cholecalciferol-oil mixture. The temperature of a chocolate base is raised to a melting point, and the cholecalciferol-oil mixture is blended into the chocolate base to form a cholecalciferol-chocolate.

18 Claims, 7 Drawing Sheets

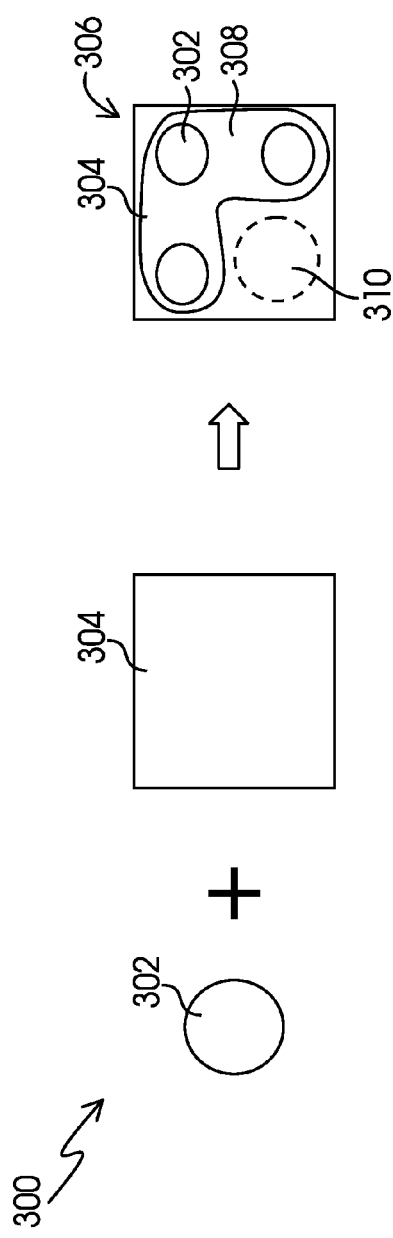
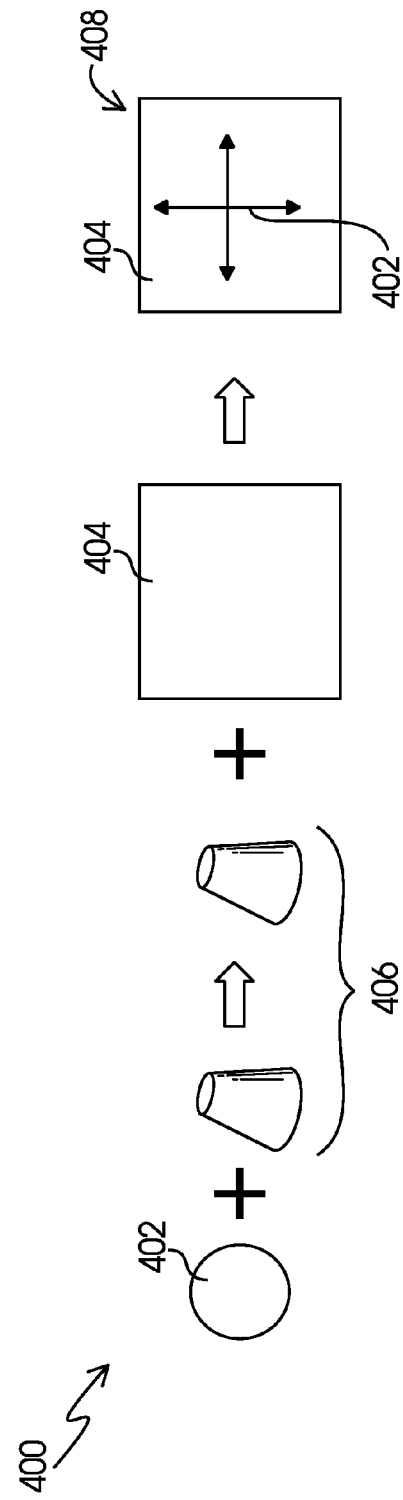
Figure 3
Figure 4

US 8,703,218 B2

CHOCOLATE HAVING CHOLECALCIFEROL AND METHOD FOR FORMING

CROSS-REFERENCE TO RELATED APPLICATIONS

The present application claims priority to U.S. Provisional Application Ser. No. 61/527,702 filed Aug. 26, 2011 and having the title "METHOD FOR INCORPORATING CHOLECALCIFEROL INTO CHOCOLATE" and U.S. Provisional Application Ser. No. 61/498,778 filed Jun. 20, 2011 and having the title "METHOD FOR DISTRIBUTING LUTEIN IN CHOCOLATE" and the subject matter of each is incorporated in their entirety herein.

BACKGROUND OF THE INVENTION

The subject matter herein relates generally to chocolate, and more particularly, to chocolate having cholecalciferol.

Many people do not receive their necessary dietary requirements through diet alone. In particular, many people do not eat foods that contain their dietary requirements because the food is not available to them, the food is too expensive, and/or the individual does not like the taste of the healthy food. Given these shortcomings, there is a need to supply essential nutrients through dietary supplements and fortified food products. Chocolate represents a desirable food base that is pleasing, inexpensive, readily available, and amenable to receive supplementation of nutrients.

However, conventional chocolates are not without their disadvantages. In particular, many dietary supplements may not be easily mixed into chocolate. For example, when trying to mix some dietary supplements with chocolate, the mixture becomes lumpy and of uneven distribution. In addition, such additions may lead to detrimental effects on chocolate tempering, which is critical to the organoleptic properties and stability of the food. Accordingly, the chocolate becomes unusable in terms of both palatability and shelf-life stability.

Additionally, despite several advances in providing chocolates with dietary supplements, vitamins such as cholecalciferol are not available in chocolate in the higher doses being recommended by recent medical guidelines. Additionally, known chocolates do not provide dietary supplements such as probiotics and lutein in combination with cholecalciferol.

A need remains for a chocolate that provides at least one of cholecalciferol, lutein, and/or probiotics in a clinically useful dose. Moreover, a need remains for a method to mix these dietary supplements evenly within chocolate at clinically meaningful doses while preserving the desirable organoleptic properties of the chocolate itself.

SUMMARY OF THE INVENTION

In one embodiment, a method for forming chocolate having cholecalciferol is provided. The method includes mixing cholecalciferol into an oil to produce a cholecalciferol-oil mixture. The temperature of a chocolate base is raised to a melting point, and the cholecalciferol-oil mixture is mixed into the chocolate base to form a cholecalciferol-chocolate.

In another embodiment, a cholecalciferol-chocolate is provided having a chocolate base and a cholecalciferol-oil mixture formed by mixing cholecalciferol into an oil. The cholecalciferol-oil mixture having been added to the chocolate base after the chocolate base has been brought to a melting point.

BRIEF DESCRIPTION OF THE DRAWINGS

The presently disclosed subject matter will be better understood from reading the following description of non-limiting embodiments, with reference to the attached drawings, wherein below:

FIG. 3 is a flowchart for a conventional process for adding lutein to chocolate without the use of oil.

FIG. 4 is a flowchart for a process for adding lutein to chocolate with the use of oil.

DETAILED DESCRIPTION OF THE DRAWINGS

The foregoing summary, as well as the following detailed description of certain embodiments will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a cholecalciferol-chocolate formed from a chocolate base and a cholecalciferol-oil mixture formed by mixing cholecalciferol into an oil, for example, vegetable oil, wherein the cholecalciferol-oil mixture is added to the chocolate base after the chocolate base has been brought to a melting point. In one embodiment, the tempered cholecalciferol-chocolate piece has a total cholecalciferol amount ranging from about 100 IU to 10,000 IU, and a total calorie range of 5 to 100 calories. In some embodiments, the cholecalciferol-chocolate may include lutein, for example, the cholecalciferol-chocolate may include lutein in a range of 0.1 to 10 mg per gram of cholecalciferol-chocolate. In one embodiment, the cholecalciferol-chocolate includes a lutein-oil mixture formed from lutein powder that has been mixed into an oil, for example, vegetable oil. The cholecalciferol-chocolate may also include probiotics, such as at least one *Lactobacillus* or *Bifidobacterium*.

Figure 1:
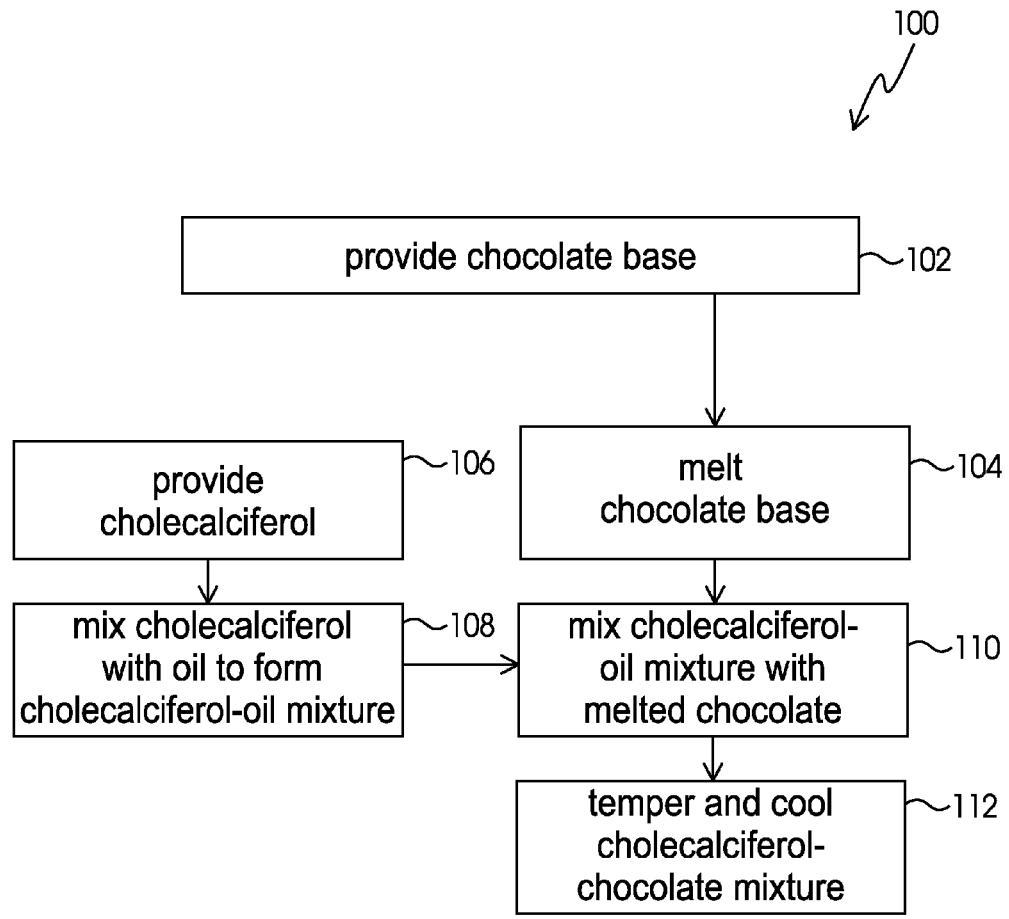
FIG. 1 is a flowchart of a method for forming a chocolate having cholecalciferol.

FIG. 1 is a flowchart for a method 100 for forming a chocolate having cholecalciferol. At step 102, a chocolate base is provided. The chocolate base may be any of unsweetened chocolate, semi-sweet chocolate, milk chocolate, dark chocolate, white chocolate, or any other suitable chocolate for forming a confection and/or chocolate drink. In one embodiment, the chocolate base may contain a high concentration of antioxidants, for example, a chocolate containing a high flavanol content, wherein a high flavanol content may be defined as 15 to 25 mg of flavanol per gram of chocolate. The chocolate base may be provided as a liquid or a solid. If the chocolate base is provided as a solid, the chocolate base is melted, at step 104, by heating the chocolate base to its respective melting point.

At step 106, cholecalciferol (vitamin D3) is provided. The cholecalciferol may be provided in a liquid form or a powder form. The cholecalciferol is mixed with oil, at step 108, to form a cholecalciferol-oil mixture. In one embodiment, the oil may be odorless food grade vegetable oil. Alternatively, the oil may be any oil suitable for forming food products. The cholecalciferol-oil mixture may have a high concentration of cholecalciferol. For example, the cholecalciferol-oil mixture may have a total cholecalciferol concentration ranging from 100,000 IU to 10,000,000 IU per gram.

At step 110, the cholecalciferol-oil mixture is mixed with the melted chocolate. Alternatively, the cholecalciferol-oil mixture may be added to the chocolate during the cooling step 112 described below. For example, the cholecalciferol-oil mixture may be blended into the melted chocolate. The fat-soluble vitamin cholecalciferol uniformly incorporates into the structure of the chocolate, which contains a fat matrix, to form cholecalciferol-chocolate. In one embodiment, the resulting tempered cholecalciferol-chocolate piece has a total cholecalciferol amount within a range of 100 IU to 10,000 IU. In another embodiment, the tempered cholecalciferol-chocolate piece has a total cholecalciferol amount of 1000 IU. The tempered cholecalciferol-chocolate piece may also have a total calorie range of 5 to 100 calories.

At step 112, the cholecalciferol-chocolate is tempered and cooled. In one embodiment, as set forth above, the cholecalciferol-oil mixture may be added to the chocolate during step 112. The cholecalciferol-chocolate may be cooled and processed to form a chocolate drink. For example, the cholecalciferol-chocolate may be cooled to a powder form that is added to a liquid to form a drink. Alternatively, the cholecalciferol-chocolate may be tempered, poured into molds, and cooled to form chocolate confections.

The method 100 may be used in the manufacturing of food items, functional foods, and confection based dietary supplements to provide a method to incorporate cholecalciferol in chocolate at a desired concentration with uniform distribution and without altering the organoleptic properties of the food or confection base. In one embodiment, the end product of the method 100 may be a chocolate having 1,000 IU of cholecalciferol in 3 grams chocolate with 15 calories. In another embodiment, the end product may be a piece of chocolate having 5,000 IU of cholecalciferol in 3 grams chocolate. In yet another embodiment, the end product may be a piece of chocolate having 10,000 IU of cholecalciferol in 3 grams of chocolate. Additional fat-soluble food additives, whether for nutritional purposes or preservation purposes, including vitamins and botanicals may also be applied by the method 100.

Figure 2:
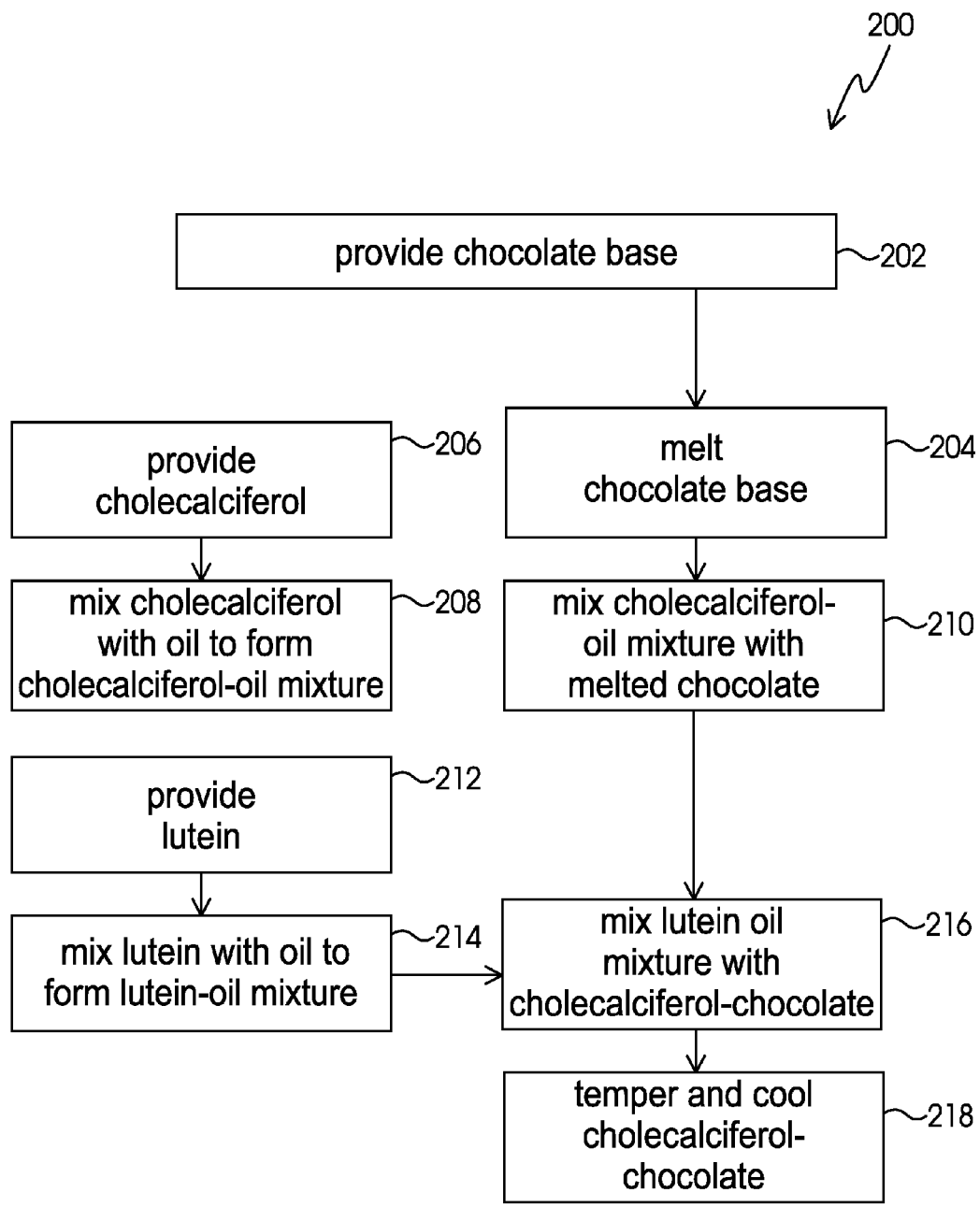
FIG. 2 is a flowchart of a method for forming a chocolate having cholecalciferol and lutein.

FIG. 2 is a flowchart for a method 200 for forming a chocolate having cholecalciferol and the dietary supplement lutein. At step 202, a chocolate base is provided. The chocolate base may be any of unsweetened chocolate, semi-sweet chocolate, milk chocolate, dark chocolate, white chocolate, or any other suitable chocolate for forming a confection and/or chocolate drink. In one embodiment, the chocolate based may be a high antioxidant chocolate, for example, a chocolate having a high flavanol content. The chocolate base may be provided as a liquid or a solid. If the chocolate base is provided as a solid, the chocolate base is melted, at step 204, by heating the chocolate base to its respective melting point.

At step 206, cholecalciferol or vitamin D3 is provided. The cholecalciferol may be provided in a liquid form or a powder form. The cholecalciferol is mixed with oil, at step 208, to form a cholecalciferol-oil mixture. In one embodiment, the oil may be odorless food grade vegetable oil. Alternatively, the oil may be any oil suitable for forming confections. The cholecalciferol-oil mixture may have a high concentration of cholecalciferol. For example, the cholecalciferol-oil mixture may have a total cholecalciferol concentration ranging from 100,000 IU to 10,000,000 IU per gram.

At step 210, the cholecalciferol-oil mixture is mixed with the melted chocolate. For example, the cholecalciferol-oil mixture may be blended into the melted chocolate. The fat-soluble cholecalciferol uniformly incorporates into the structure of the chocolate, which contains a fat matrix, to form cholecalciferol-chocolate. In one embodiment, the tempered cholecalciferol-chocolate piece has a total cholecalciferol amount within a range of 100 IU to 10,000 IU.

At step 212, lutein is provided in a powder form. At step 214, the lutein is added to oil. For example, the lutein may be added to odorless food grade vegetable oil. Alternatively, the lutein may be added to any suitable oil for forming food products. The lutein and oil are then mixed until the lutein powder incorporates substantially evenly in the vegetable oil to form a lutein-oil mixture. The percentage by weight of lutein to the total weight of the lutein-oil mixture may be 1% to 80%. At step 216, the lutein-oil mixture is added to the cholecalciferol-chocolate to form a lutein-oil-chocolate mixture. The percentage by weight of the lutein to the finished lutein-oil-chocolate mixture may be 0.001% to 10%. For example, the total amount of lutein in the lutein-oil-chocolate mixture may be within a range of 0.1 to 10 mg per gram of lutein-oil-chocolate mixture.

In one embodiment, the lutein-oil mixture may be added during the melting cycle of a chocolate manufacturing process. According to another embodiment, the lutein-oil mixture may be added during any other cycles of a chocolate manufacturing process, for example the tempering cycle, the molding cycle, or the cooling cycle.

At step 218, the cholecalciferol-chocolate is tempered and cooled. In one embodiment, the cholecalciferol-oil mixture may be added to the chocolate during step 218. The cholecalciferol-chocolate may be cooled and processed to form a chocolate drink. For example, the cholecalciferol-chocolate may be cooled to a powder form that is added to a liquid to form a drink. Alternatively, the cholecalciferol-chocolate may be tempered, poured into molds, and cooled to form chocolate confections. In one embodiment, the cholecalciferol-chocolate may contain approximately 2.5 mg of lutein per 9 gram piece of chocolate.

The method 200 avoids the problems of adding lutein powder directly into liquefied chocolate. Directly adding lutein powder into liquefied chocolate often causes the lutein to clump inside the chocolate. The lutein clumps give the chocolate unfavorable organoleptic properties that can be detected by an individual when ingesting the chocolate. In addition, such clumping may result in non-uniform distribution of lutein which may lead to individual pieces of tempered chocolate having non-uniform concentrations of lutein. The lutein-oil-chocolate mixture created by the method 200 provides for a homogenous distribution of lutein of a particle size smaller than the human sensory threshold for the alteration of organoleptic properties of chocolate.

The method 200 may be used in the manufacturing of food items, functional foods, and confection based dietary supplements to provide a method to incorporate lutein in chocolate at a desired concentration with uniform distribution and without altering the organoleptic properties of the lutein. In one embodiment, an end product of the method 200 may be a chocolate having 500 IU of cholecalciferol in a 9 gram chocolate with 2.5 mg lutein and high flavanol chocolate base. Additional fat-soluble food additives, whether for nutritional purposes or preservation purposes, including vitamins and botanicals may also be applied by the method 200.

FIG. 3 is a flowchart 300 for a conventional process for adding lutein 302 to chocolate 304 without the use of oil. As illustrated, lutein 302 is conventionally added directly to chocolate 304 in a powder form. Typically, the powdered lutein 302 does not evenly distribute within the chocolate 304 and forms clumps within the chocolate 304, as illustrated by the lutein-chocolate 306. Accordingly, some portions 308 of the lutein-chocolate 306 include lutein 302, whereas some portions 310 of the lutein-chocolate 306 are devoid of lutein 302.

FIG. 4 is a flowchart 400 for a process for adding lutein 402 to chocolate 404 with the use of oil 406. The lutein 402 is mixed into the oil 406 so that the lutein 402 becomes evenly distributed within the oil 406. The lutein-oil mixture is then added to the chocolate 404 so that the lutein 402 is evenly distributed in a lutein-chocolate 408. Accordingly, in contrast to the lutein-chocolate 306 (shown in FIG. 3), each portion of the lutein-chocolate 408 includes lutein 402.

Figure 5:
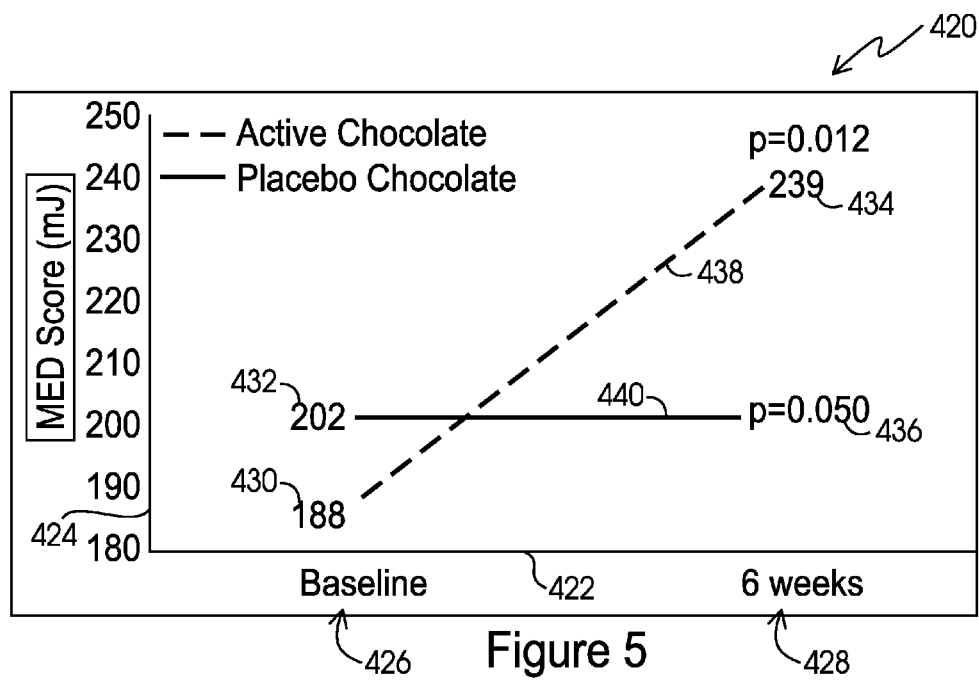
FIG. 5 is a graph showing the results of clinical trials using the chocolate described in FIG. 2.

FIG. 5 is a graph 420 of data showing the results of clinical trials using a cholecalciferol-chocolate formed by the method 200. The graph 420 shows the results of a minimal erythema dose (MED) test, which determines the amount of ultraviolet B (UVB) light required to cause erythema on the skin. The x-axis 422 illustrates time in weeks, and the y-axis 424 illustrates an MED score. Ten subjects were tested. Five of the subjects were given chocolate with cholecalciferol, lutein, and high flavanol content (active chocolate). Five subjects were given normal dark chocolate with comparably low flavanol (placebo chocolate). The test was randomized and double blind.

At day zero 426, a baseline score was taken for each of the ten subjects. The five subjects given the active chocolate had an average baseline score 430 of 188. The five subjects given the placebo chocolate had an average baseline score 432 of 202. After six weeks 428, the ten subjects were tested again. The five subjects given the active chocolate had an average score 434 of 239. Accordingly, the line 438 representing the active chocolate had a p-value of 0.012. The five subjects given the placebo chocolate had an average score 436 of 202. Accordingly, the line 440 representing the placebo chocolate had a p-value of 0.50.

Based on the test results, the people taking the active chocolate needed more UVB light to cause the same erythema, indicating that the active chocolate was protective against UV damage. The placebo chocolate did not have the same benefits.

Figure 6:
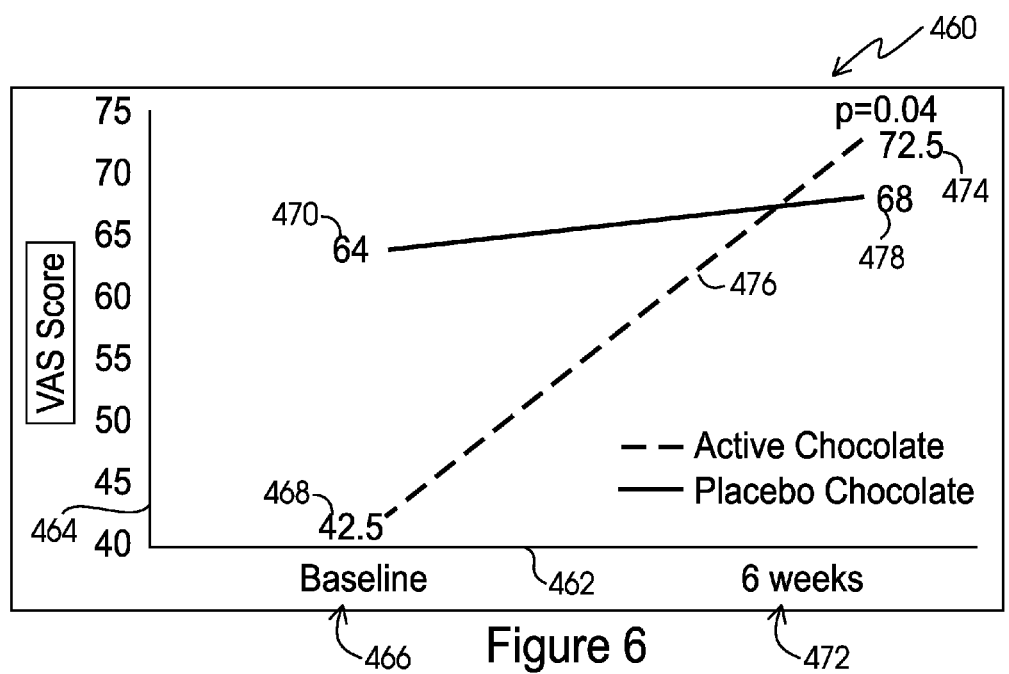
FIG. 6 is another graph showing the results of clinical trials using the chocolate described in FIG. 2.

FIG. 6 is a visual analog graph 460 showing the results of clinical trials using a cholecalciferol-chocolate formed by the method 200. The graph 460 illustrates a visual analog scale for skin appearance. The x-axis 462 illustrates time in weeks, and the y-axis 464 illustrates a visual analog score for overall skin appearance, wherein a score of zero is the worst skin appearance and a score of 100 is the best skin appearance. Eight subjects were tested. Four of the subjects were given chocolate with cholecalciferol, lutein, and high flavanol content (active chocolate). Four subjects were given normal dark chocolate with comparably low flavanol (placebo chocolate). The test was randomized and double blind.

At day zero 466, a baseline score was taken for each of the eight subjects. The four subjects given the active chocolate had an average baseline score 468 of 42.5. The four subjects given the placebo chocolate had an average baseline score 470 of 64. After six weeks 472, the eight subjects were tested again. The four subjects given the active chocolate had an average score 474 of 72.5. Accordingly, the line 476 representing the active chocolate had a p-value of 0.04. The four subjects given the placebo chocolate had an average score 478 of 68. Accordingly, the line 480 representing the placebo chocolate had a p-value of approximately 0.5.

Based on the test results, subjects taking the active chocolate had a self-reported improvement in skin appearance. Subjects taking the placebo chocolate did not have the same benefits.

Figure 7:
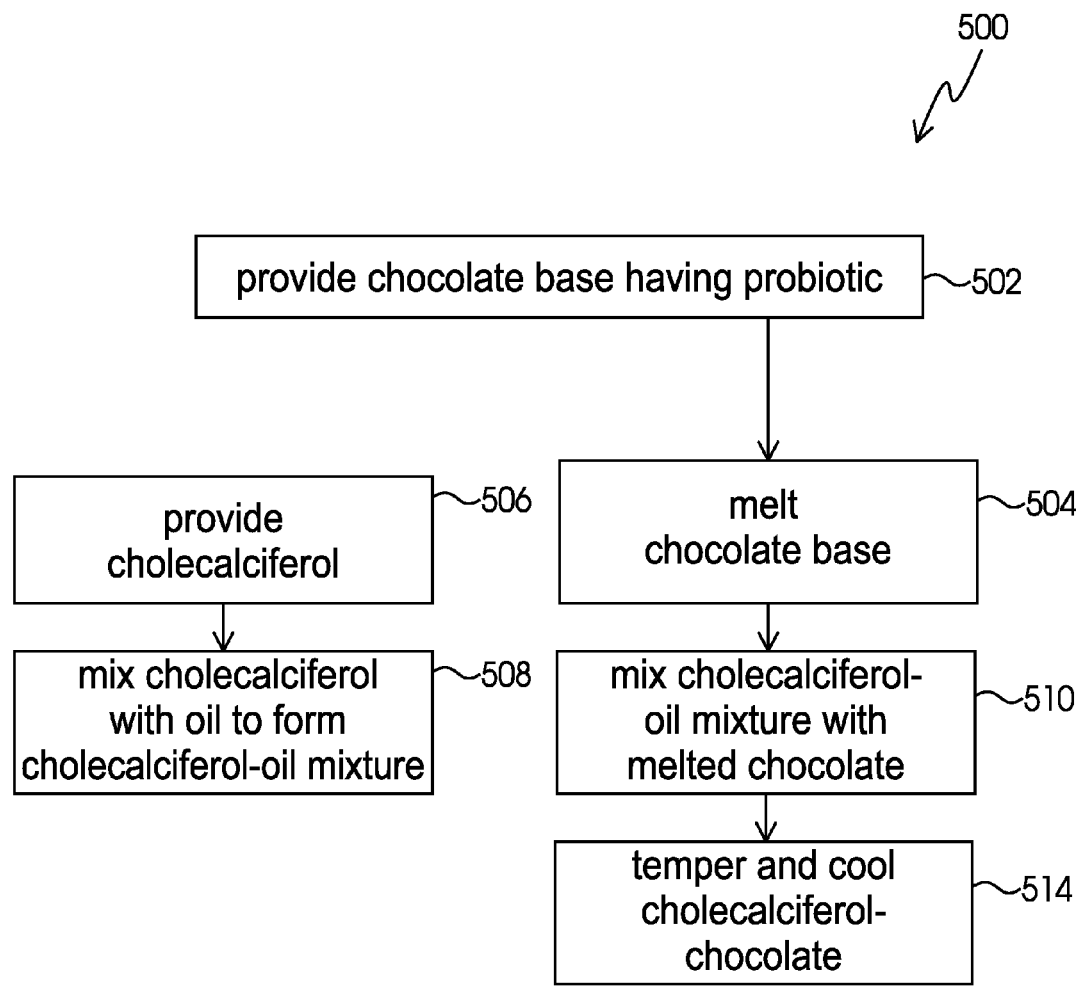
FIG. 7 is a flowchart of a method for forming a chocolate having cholecalciferol and probiotics.

FIG. 7 is a flowchart for a method 500 for forming a chocolate having cholecalciferol and probiotics. At step 502, a chocolate base is provided. The chocolate base may be any of unsweetened chocolate, semi-sweet chocolate, milk chocolate, dark chocolate, white chocolate, or any other suitable chocolate for forming a confection and/or chocolate drink. In one embodiment, the chocolate based may be a high antioxidant chocolate, for example, a chocolate containing a high flavanol content. The chocolate base may be provided as a liquid or a solid. In one embodiment, the chocolate base includes a probiotic. In one embodiment, the probiotic may be at least one species from *Lactobacillus* or *Bifidobacterium*. Alternatively, the probiotic may be any other probiotic suitable for use in a food product. The probiotic may be microencapsulated before addition to the chocolate base. If the chocolate base is provided as a solid, the chocolate base is melted, at step 504, by heating the chocolate base to its respective melting point.

At step 506, cholecalciferol or vitamin D3 is provided. The cholecalciferol may be provided in a liquid form or a powder form. The cholecalciferol is mixed with oil, at step 508, to form a cholecalciferol-oil mixture. In one embodiment, the oil may be odorless food grade vegetable oil. Alternatively, the oil may be any oil suitable for forming confections. The cholecalciferol-oil mixture may have a high concentration of cholecalciferol. For example, the cholecalciferol-oil mixture may have a total cholecalciferol concentration ranging from 100,000 IU to 10,000,000 IU per gram.

At step 510, the cholecalciferol-oil mixture is mixed with the melted chocolate. For example, the cholecalciferol-oil mixture may be blended into the melted chocolate. The fat-soluble cholecalciferol uniformly incorporates into the structure of the chocolate, which contains a fat matrix, to form cholecalciferol-chocolate. In one embodiment, the tempered cholecalciferol-chocolate piece has a total cholecalciferol amount within a range of 100 IU to 10,000 IU. In one embodiment, if the probiotic is not provided in the chocolate, the probiotic may be added to the chocolate with the cholecalciferol at the chocolate tempering phase. According to other embodiments, the probiotic and cholecalciferol may be added during any other cycles of a chocolate manufacturing process, for example the melting cycle, the molding cycle, or the cooling cycle.

At step 514, the cholecalciferol-chocolate is tempered and cooled. In one embodiment, the cholecalciferol-chocolate may be cooled and processed to form a chocolate drink. For example, the cholecalciferol-chocolate may be cooled to a powder form that is added to a liquid to form a drink. Alternatively, the cholecalciferol-chocolate may be tempered, poured into molds, and cooled to form chocolate confections.

The method 500 may be used in the manufacturing of food items, functional foods, and confection based dietary supplements to provide a method to incorporate probiotics in chocolate at a desired concentration with uniform distribution and without altering the organoleptic properties of the food or confection base. In one embodiment, an end product of the method 500 may be a chocolate having 1,000 IU of cholecalciferol in 10 grams of chocolate with a mixture of one-half billion *Lactobacillus Helveticus* and *Bifidobacterium Longum* species. Alternatively, the chocolate may include a range of 100 million to 5 billion probiotic organisms per 10 grams of chocolate. Additional fat-soluble food additives, whether for nutritional purposes or preservation purposes, including vitamins and botanicals may also be applied by the method 500.

Figure 8:
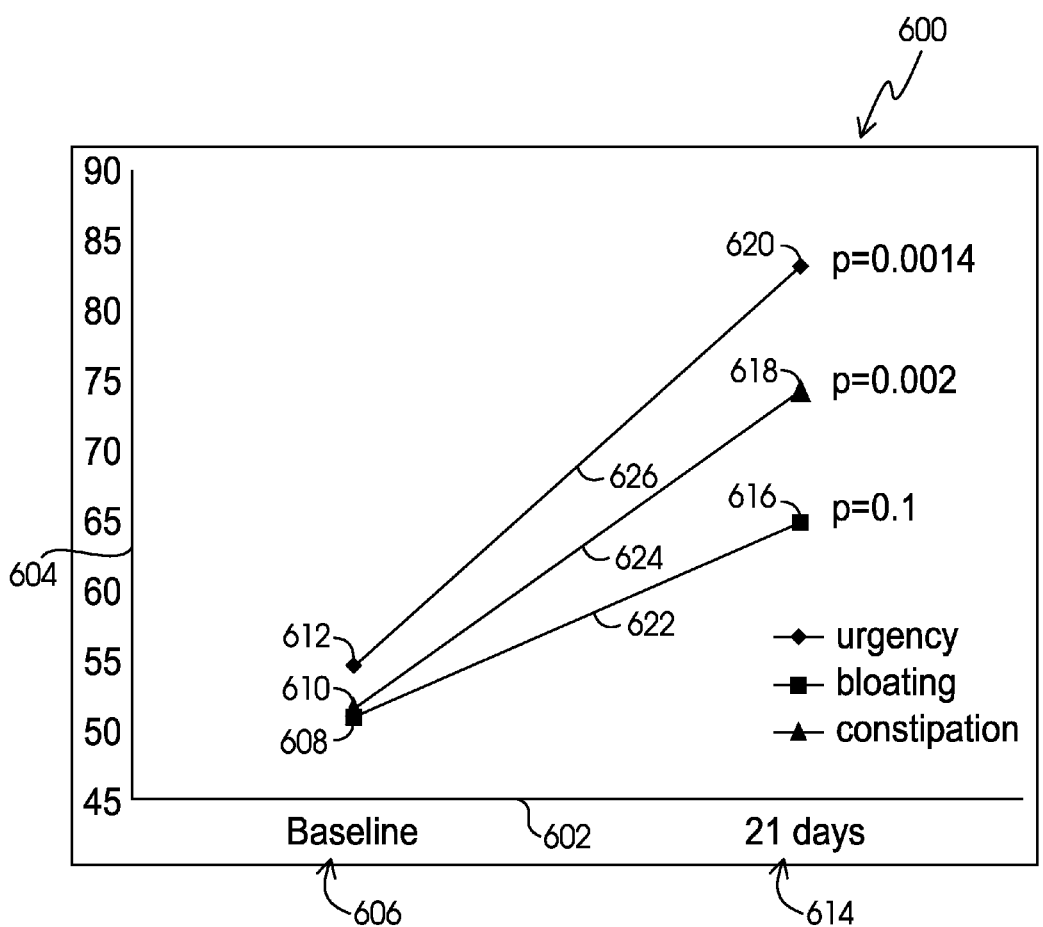
FIG. 8 is a graph of a visual analog scale showing the results of clinical trials using the chocolate described in FIG. 5.

FIG. 8 is a visual analog graph 600 showing the results of clinical trials using the chocolate described in FIG. 5. The x-axis 602 illustrates time in days. The y-axis 604 illustrates a pain scale from 0 to 100, wherein 0 represents the worst pain and 100 represents no pain. Fourteen people who regularly experienced gastrointestinal symptoms were surveyed at least once per week regarding their digestive symptoms. The gastrointestinal symptoms surveyed included urgency, bloating, and constipation.

A baseline 606 score was taken on day 0. At baseline, the average survey result 608 for bloating was approximately 51 on the pain scale. The average survey result 610 for constipation was also approximately 51. Further, the average survey result 612 for urgency was approximately 55.

A final survey 614 was taken after 21 days. At the final survey, the average survey result 616 for bloating was approximately 63 on the pain scale. The average survey result 618 for constipation was approximately 73. Further, the average survey result 620 for urgency was approximately 84.

Accordingly, on average each patient experienced improvements in their gastrointestinal symptoms. For example, the line 622 representing changes in bloating has a p value of 0.1. Additionally, the line 624 representing changes in constipation has a p value of 0.002. Further, the line 626 representing changes in urgency has a p value of 0.0014. According to clinical standards, the p values show statistical significances for urgency, bloating, and constipation.

Figure 9:
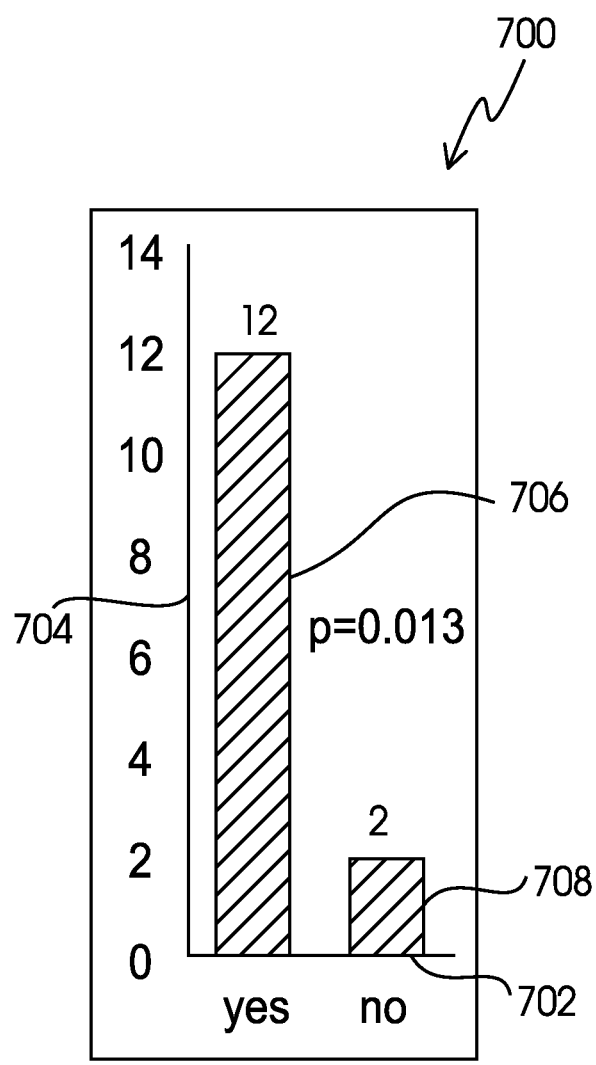
FIG. 9 is a graph showing improvements in common digestive symptoms when using the chocolate described in FIG. 5.

FIG. 9 is a graph 700 showing improvements in common digestive symptoms when using the chocolate described in FIG. 5. The x-axis 702 represents the results of a yes/no survey study where subjects were asked, "Do you feel that this chocolate improved your symptoms of bowel inconsistency and bloating?". The y-axis 704 represents the number of participants in the study. Each participant took the chocolate described in FIG. 5 for three weeks. Of the 14 participants, 12 participants who took the chocolate reported an improvement in the symptoms of bowel inconsistency and bloating, as illustrated by the bar 706. 2 participants reported that the chocolate did not help alleviate symptoms, as illustrated by the bar 708. Accordingly, the test showed a p value of 0.013 which is considered strongly statistically significant.

In one embodiment, the various embodiments provide a method for forming chocolate having cholecalciferol. The method includes mixing cholecalciferol into an oil, for example, vegetable oil, to produce a cholecalciferol-oil mixture. The temperature of a chocolate base is then raised to a melting point, and the cholecalciferol-oil mixture is mixed into the chocolate base to form a cholecalciferol-chocolate. In one embodiment, the cholecalciferol-chocolate has a cholecalciferol amount ranging from about 500 IU to 10,000 IU per chocolate piece, and a calorie range of 5 to 100 calories per gram of chocolate. In some embodiments the method includes mixing lutein into the cholecalciferol-chocolate, for example, mixing lutein into the cholecalciferol-chocolate in a concentration range of 0.1 to 10 mg per gram of chocolate. In one embodiment, lutein powder is added into an oil, for example, vegetable oil, and is mixed to form a lutein-oil mixture. The lutein-oil mixture is mixed into the cholecalciferol-chocolate. In another embodiment, probiotics, such as *Lactobacillus* and/or *Bifidobacterium* are mixed into the cholecalciferol-chocolate.

The embodiments described herein provide a chocolate having at least one of cholecalciferol, lutein, and/or probiotics. Moreover, the embodiments described herein provide a method for mixing dietary supplements evenly within chocolate. For example, the embodiments described herein provide a method for incorporating cholecalciferol at a desired concentration with uniform distribution within chocolate without altering the organoleptic properties of the chocolate. Moreover, the embodiments described herein provide a homogenous distribution of lutein within chocolate, wherein the lutein has a particle size smaller than the human sensory threshold for the alteration of organoleptic properties of chocolate.

Exemplary embodiments of a cholecalciferol-chocolate and a method for forming a cholecalciferol-chocolate are described above in detail. The components and method steps illustrated are not limited to the specific embodiments described herein, but rather, the components and method steps may be utilized independently and separately from other components described herein. For example, the method steps and components described in each of FIGS. 1, 2, and 5 may also be used in combination with each other.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for forming a chocolate having cholecalciferol, the method comprising:
   raising the temperature of a chocolate base to a melting point;
   mixing cholecalciferol into an oil to produce a cholecalciferol-oil mixture; wherein the oil is not from the chocolate base; and
   mixing the cholecalciferol-oil mixture into the chocolate base to form a cholecalciferol-chocolate.

2. The method of claim 1 further comprising forming a cholecalciferol-chocolate piece having a total cholecalciferol amount ranging from about 100 IU to 10,000 IU.

3. The method of claim 1 further comprising forming a cholecalciferol-chocolate piece having a total calorie range of 5 to 100 calories.

4. The method of claim 1 further comprising:
   adding lutein powder into an additional oil;
   mixing the lutein powder and the additional oil to form a lutein-oil mixture; and
   adding the lutein-oil mixture into the cholecalciferol-chocolate.

5. The method of claim 4 further comprising mixing lutein into the cholecalciferol-chocolate in a concentration range of 0.1 to 10 mg per gram of cholecalciferol-chocolate.

6. The method of claim 1, wherein the oil is vegetable oil.

7. The method of claim 1 further comprising providing the chocolate base having probiotics.

8. The method of claim 1 further comprising providing the chocolate base having at least one of *Lactobacillus* or *Bifidobacterium*.

9. The method of claim 1, wherein the chocolate base is a high antioxidant chocolate and wherein the high antioxidant chocolate is defined as having 15 to 25 mg of flavonol content per gram of chocolate.

10. The method of claim 4, wherein the additional oil is vegetable oil.

11. The method of claim 4 further comprising providing the chocolate base having probiotics.

12. The method of claim 4 further comprising providing the chocolate base having at least one of *Lactobacillus* or *Bifidobacterium*.

13. The method of claim 4, wherein the chocolate base is a high antioxidant chocolate and wherein the high antioxidant chocolate is defined as having 15 to 25 mg of flavonol content per gram of chocolate.

14. A method for forming a chocolate having cholecalciferol, the method comprising:
   raising the temperature of a chocolate base to a melting point;
   mixing cholecalciferol into an oil to produce a cholecalciferol-oil mixture; wherein the oil that is not the chocolate base;
   mixing the cholecalciferol-oil mixture into the chocolate base;
   wherein the chocolate base has probiotics;
   wherein the cholecalciferol-oil uniformly incorporates into the structure of the chocolate to form a cholecalciferol-chocolate; and
   wherein the organoleptic properties of the chocolate base are not altered with the incorporation of the cholecalciferol into the chocolate base.

15. The method of claim 14 further comprising providing the chocolate base having at least one of *Lactobacillus* or *Bifidobacterium*.

16. The method of claim 15, wherein the chocolate base is a high antioxidant chocolate and wherein the high antioxidant chocolate is defined as having 15 to 25 mg of flavonol content per gram of chocolate.

17. The method of claim 16 further comprising mixing lutein into the cholecalciferol-chocolate in a concentration range of 0.1 to 10 mg per gram of cholecalciferol-chocolate.

18. The method of claim 16 further comprising:
   adding lutein powder into an additional oil;
   mixing the lutein powder and the additional oil to form a lutein-oil mixture; and
   adding the lutein-oil mixture into the cholecalciferol-chocolate.

* * * * *